United States Patent
Burch

[19]

[11] Patent Number: 5,944,013
[45] Date of Patent: Aug. 31, 1999

[54] RESUSCITATOR

[76] Inventor: John M. Burch, 2512 Horseman, Plano, Tex. 75025

[21] Appl. No.: 09/209,945

[22] Filed: Dec. 11, 1998

[51] Int. Cl.$^6$ .................................................. A62B 7/00
[52] U.S. Cl. ............................ 128/205.14; 128/203.11; 128/205.11; 128/205.25; 128/206.15; 128/207.12
[58] Field of Search ................. 128/202.28, 202.29, 128/203.11, 205.11, 205.14, 205.25, 206.15, 207.12

[56] References Cited

U.S. PATENT DOCUMENTS

| | | | |
|---|---|---|---|
| 3,046,978 | 7/1962 | Lea | 128/205.13 |
| 3,850,171 | 11/1974 | Ball et al. | 128/205.11 |
| 4,037,595 | 7/1977 | Elam | 128/205.11 |
| 4,226,234 | 10/1980 | Gunderson | 128/207.12 |
| 4,266,540 | 5/1981 | Panzik et al. | 128/207.12 |
| 4,655,213 | 4/1987 | Rapoport et al. | 128/207.12 |
| 4,782,831 | 11/1988 | Gallant | 128/205.24 |
| 4,821,713 | 4/1989 | Bauman | 128/205.13 |
| 5,301,667 | 4/1994 | McGrail et al. | 128/205.14 |
| 5,427,091 | 6/1995 | Phillips | 128/202.28 |
| 5,520,173 | 5/1996 | Kuhn | 128/205.13 |
| 5,537,999 | 7/1996 | Dearman et al. | 128/205.14 |
| 5,645,056 | 7/1997 | Pomeroy | 128/205.14 |
| 5,722,394 | 3/1998 | Loescher | 128/203.11 |
| 5,813,423 | 9/1998 | Kirchgeorg | 128/202.28 |

*Primary Examiner*—Aaron J. Lewis
*Attorney, Agent, or Firm*—Anderson, Levine & Lintel, L.L.P.

[57] ABSTRACT

A manual resuscitator controls the portion of gas delivered from the ventilation bag to the patient responsive to which of a plurality of masks the ventilation bag is connected. Different sized masks deliver different portions of the gas from the ventilation bag as would be appropriate for a patient of a size associated with the mask. Emergency personnel, or others, need only couple the correct size mask to the ventilation bag, and the correct volume of gas is automatically delivered to the patient.

20 Claims, 5 Drawing Sheets

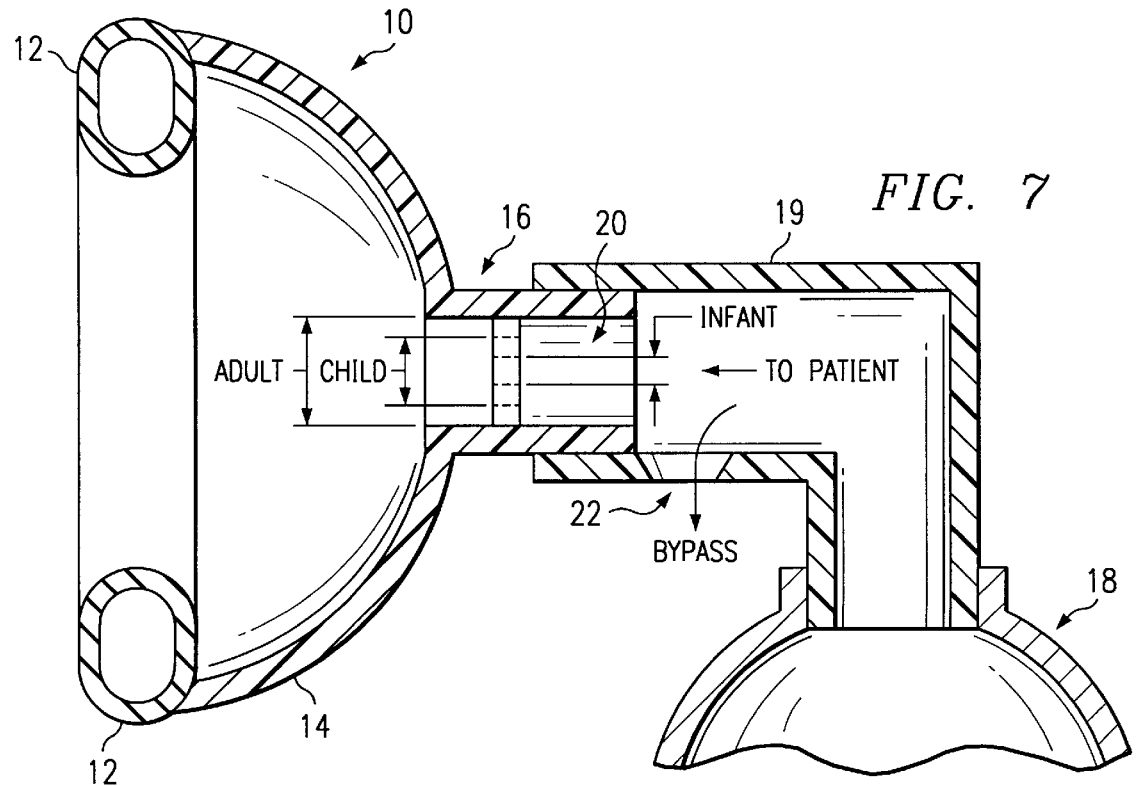
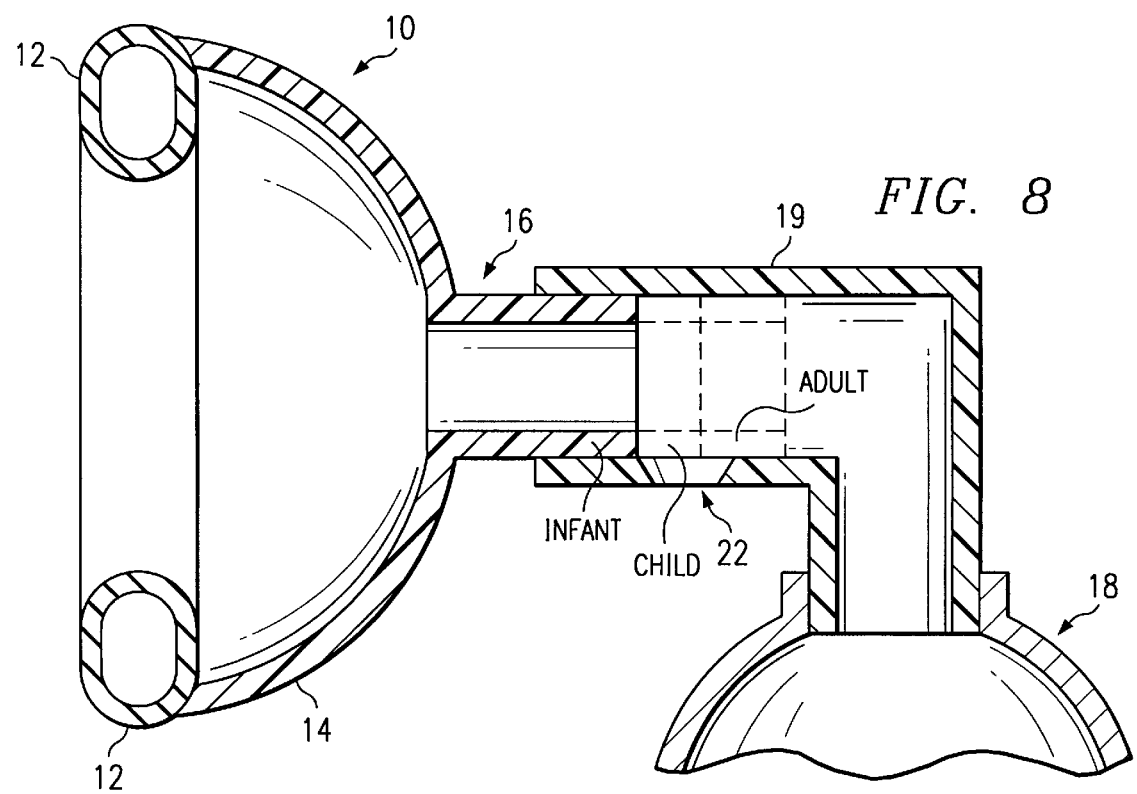

RESUSCITATOR

CROSS-REFERENCE TO RELATED APPLICATIONS

Not Applicable

STATEMENT OF FEDERALLY SPONSORED RESEARCH OR DEVELOPMENT

Not Applicable

BACKGROUND OF THE INVENTION

1. Technical Field

This invention relates in general to resuscitators and, more particularly, to a resuscitation system for use with various patient sizes.

2. Description of the Related Art

Emergency medical personnel, and others, are often called upon to ventilate patients who have stopped breathing. Loss of spontaneous breathing can occur in many situations, particularly in drowning situations, asthma, allergic reations, cardiopulmonary arrest and respiratory arrest. Once spontaneous breathing has stopped, it is imperative to restore breathing as soon as possible, but until that can be accomplished, emergency personnel must breathe for the patient.

In many situations, mouth-to-mouth resuscitation is used to restore normal breathing in a patient or is used to artificially breathe for a patient. Mouth-to-mouth resuscitation has several drawbacks, including contact with the body fluids of a stranger. Therefore, manual resuscitators have been developed. A manual resuscitator is used with a face mask or endotracheal tube and an inflatable ventilation bag. The ventilation bag is typically filled with air from the surrounding atmosphere or with oxygen (or oxygen-rich air) from a supply tank. With the face mask covering the patient's mouth and nose, the operator squeezes the ventilation bag, forcing the air/oxygen in the ventilation bag into the patient's lungs. As the ventilation bag is released, the patient exhales, and the ventilation bag is refilled with air/oxygen. The operator can continue this cycle until the patient begins spontaneous breathing without external aids, or until such time that the patient can be aided by an automatic resuscitator.

On each pump cycle, as the air/oxygen is pumped into the patient's lungs, it is important that the correct amount of air/oxygen be applied. For an adult, the ventilation bag generally expels between 1500 and 2000 cc of air/oxygen. For a child, only 600–750 cc are expelled and for pediatrics, only 200 cc are expelled. If an operator squeezed the full amount of an adult ventilation bag into a child patient, the child's lungs would likely burst.

One solution is to include a safety release valve on the mask which will open if the pressure inside the mask exceeds a certain level. The safety release valve, while beneficial in some cases, may fail to open in time to prevent serious injury, and is therefore not entirely reliable.

The use of a single resuscitation device to accommodate the lung sizes of different age classes has been the subject of several patents. In U.S. Pat. No. 3,046,978 to Lea, a ventilation bag with markings for different age groups is provided, whereby the volume of air delivered to the patient varies depending upon where the ventilation bag is squeezed. U.S. Pat. No. 5,520,173 to Kuhn offers a similar solution hereby the ventilation bag has gripping sections with varying cross-sections for each age group. In U.S. Pat. No. 5,301,667 to McGrail et al, a pressure limiting valve can be set at various positions to control the pressure of the ventilation gas applied to the patient. Similarly, U.S. Pat. No. 4,821,713 provides a rotatable cap with various vent openings which can be positioned to accommodate various age groups. U.S. Pat. No. 5,645,056 describes an air bag having a volume which is constricted by a belt which can be tightened according to the patient's weight.

While these aforementioned devices address the need for different gas volume levels for different patients, they all suffer from a significant flaw. Under the stress of an emergency, all of these devices could be misused, resulting in catastrophic damage to a patient's lungs. When time is of the essence, less experienced persons, such as lifeguards or family members, and even experienced emergency medical personal, can miss a required setting or squeeze at the wrong place on the ventilation bag.

Accordingly, most emergency medical crews carry separate devices for each age class in the emergency vehicles. Because of space considerations, however, only the device size needed is packed in the emergency kit taken to the scene. The emergency medical crews pack the device based on information from a dispatcher. This can often lead to problems, as inaccurate communications often occur between the person who called for help and the dispatcher or between the dispatcher and the emergency medical personnel. For example, the dispatcher may communicate the patient is a eighteen year old, where, in fact, the patient is a eight year old. Similarly, the dispatcher may report that the patient is a sixteen year old, where, in fact, the patient is a sixteen month old. In these cases, the emergency medical personnel must return to the vehicle to get the properly sized equipment, wasting precious time.

Therefore, a need has arisen for a method and apparatus for effectively resuscitating a patient of arbitrary size.

BRIEF SUMMARY OF THE INVENTION

A manual resuscitation system includes a ventilation bag which holds a known volume of a gas and a plurality of masks of different sizes for individually coupling to said ventilation bag, each of the masks sized to fit an associated patient size, wherein the amount of gas transmitted to a patient responsive to the ventilation bag being squeezed is dependent upon which of said masks is coupled to said ventilation bag.

The present invention provides significant advantages over the prior art. The plurality of masks can fit, for example, infant, child and adult patients, respectively. A single ventilation bag, with a plurality of masks, can be taken together to the scene of an emergency, requiring very little space. The mask that fits the patient will automatically pass the correct volume of gas, without any adjustment on the part of the operator. Therefore, there is very little chance that the manual resuscitator will force too much gas into the lungs of the patient.

BRIEF DESCRIPTION OF THE SEVERAL VIEWS OF THE DRAWINGS

For a more complete understanding of the present invention, and the advantages thereof, reference is now made to the following descriptions taken in conjunction with the accompanying drawings, in which:

FIG. 7 illustrates a cross-sectional view of a first alternative embodiment of a mask which controls the flow of gas from a ventilation bag; and FIG. 8 illustrates a cross-sectional view of a second alternative embodiment of a mask which controls the flow of gas from a ventilation bag.

DETAILED DESCRIPTION OF THE INVENTION

The present invention is best understood in relation to FIGS. 1–8 of the drawings, like numerals being used for like elements of the various drawings.

Figure 1:
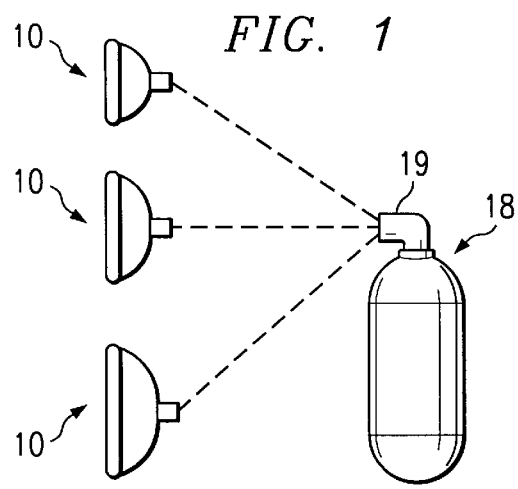
FIG. 1 illustrates a diagram of the invention using three masks and a ventilation bag.

FIG. 1 illustrates a diagram of the present invention. In a situation where a patient must be ventilated, one of a set of masks 10 (for example, a set of infant, child and adult masks) can be selectively coupled to a ventilation bag 18. The mask which is coupled to the ventilation bag controls whether the patient receives all or a portion of the gas in the ventilation bag 18 as the bag is squeezed. Accordingly, by selecting the proper size mask, the correct volume is likewise selected, avoiding problems with excessive volume.

The ventilation bag 18 can be of conventional design. It is assumed herein that the ventilation bag 18 includes the mechanism for refilling the bag with air or other gas after each squeeze. In general, the ventilation bag 18 and masks 10 are disposable.

Figure 2:
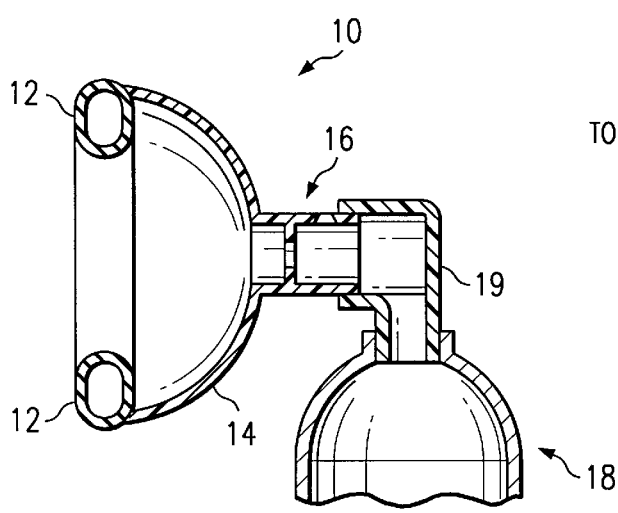
FIG. 2 illustrates a cross-sectional view of a mask which controls the volume of gas from a ventilation bag which passes to the patient.

FIG. 2 illustrates a first embodiment of the invention where in the amount of gas delivered to a patient responsive to a pumping of the ventilation bag is controlled by the mask. In FIG. 2, each mask 10 includes a seal 12, a face plate 14 and an interface 16 for connecting the mask to a ventilation bag 18 via a swiveling elbow joint 19. The interface 16 may include a flow-through valve 20 and a bypass valve 22.

In the preferred embodiment, the ventilation bag is a standard ventilation bag, capable of delivering the correct volume of air for an adult, i.e., between 1500 and 2000 cc of air/oxygen, on a single pump. The interface 16 for each mask determines the portion of the air/oxygen from the ventilation bag 18 which is delivered to the patient. In the illustrated embodiment, the interface contains a flow-through valve 20 and a bypass valve 22. The relative sizes of the flow-through valve 20, which transmits gas from the ventilation bag 18 to the patient and the bypass valve 22 determines what portion of the gas is passed to the patient. Increasing the opening in the flow-through valve 20 relative to the bypass valve 22 will increase the portion of gas delivered to the patients lungs responsive to a squeeze of the ventilation bag, since less gas from the ventilation bag 18 will flow-through the bypass valve 22 into the atmosphere. Conversely, decreasing the size of the opening in the flow-through valve 20 relative to the bypass valve 22 will decrease the portion of the gas delivered to the patient's lungs, since the amount of gas from the ventilation bag 18 which will pass through the bypass valve 22 into the atmosphere will increase.

Each mask in a set of masks has a different ratio of the sizes of the flow through valve 20 and the bypass valve 22. Thus, while the amount of gas leaving the ventilation bag on each squeeze is consistent, the amount of gas reaching the patient is dependent upon which mask is coupled to the ventilation bag.

Figure 3A:
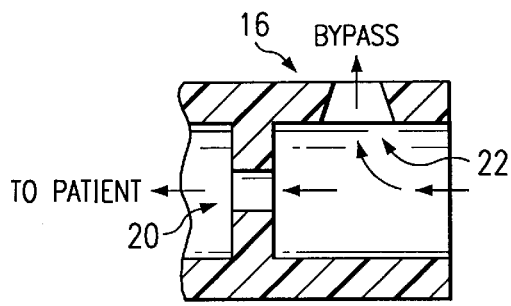
FIGS. 3a through 3c illustrate cross-sectional views of interfaces used in a first embodiment of a set of masks according to FIG. 2.
Figure 3B:
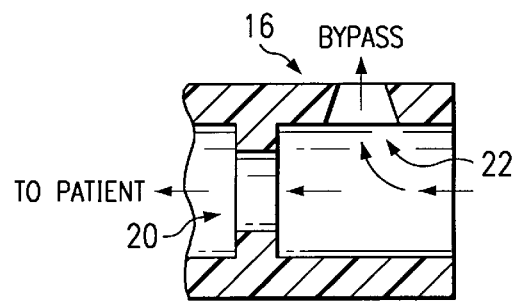
Figure 3C:
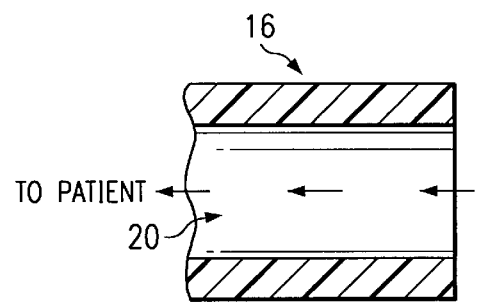

FIGS. 3a–c illustrate examples of interfaces 16 for an infant, child and adult, respectively. For a ventilation bag which delivers 1500–2000 cc of gas, the combination of flow-through valve 20 and bypass valve 22 for an infant, shown in FIG. 3a, should pass about 10% of the gas from the ventilation bag 18 to the patient. The combination of flow-through valve 20 and bypass valve 22 for an child, shown in FIG. 3b, should pass about 40% of the gas from the ventilation bag 18 to the patient. The interface 16 for an adult passes all of the gas from the ventilation bag 18 to the patient.

In operation, when a patient needs to be manually resuscitated, the emergency personnel, or other person, attaches the mask which fits the patient appropriately to the ventilation bag. The interface 16 on that mask 10 automatically delivers the correct volume of air from the ventilation bag 18 to the patient with a full squeeze of the bag. A mask which is too big will not seal with the patient, and therefore cannot create a problem of over-ventilating the patient.

While the embodiment shown in FIGS. 3a–c illustrates three mask sizes, infant, child and adult, more masks could be used in a set. For example, masks could be designated 0–1 year, 1–3 years, 3–8 years, and so on. Alternatively, masks could be classified by weight. While more masks would provide a smoother continuum of air volumes between masks, the greater number of masks is more likely to cause confusion at the scene of an emergency and will require more space in the emergency kit.

Figure 4:
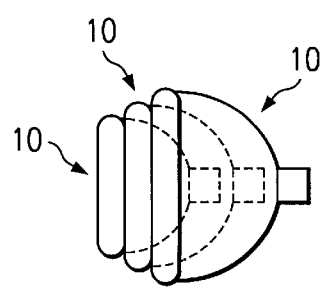
FIG. 4 illustrates a set of nested masks.

FIG. 4 illustrates multiple masks 10, stored in a nested configuration along with the ventilation bag 18. By designing the masks 10 to nest, the complete resuscitation system is no greater in size than a normal manual resuscitator for a single patient size.

Figure 5A:
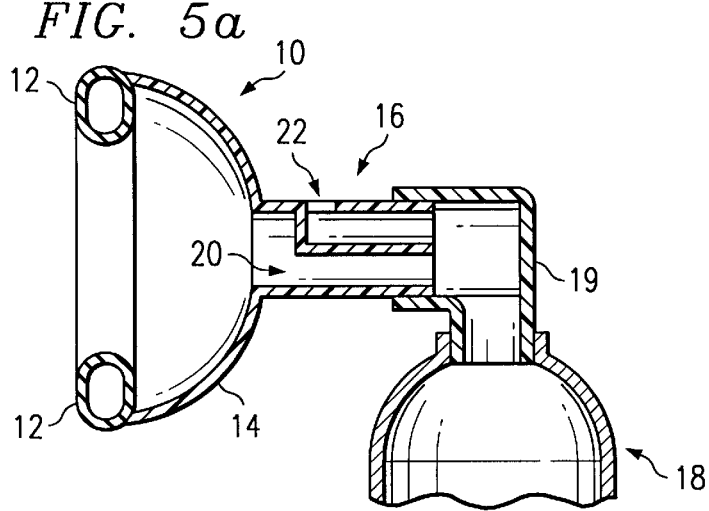
FIGS. 5a through 5f illustrate cross-sectional and front views of interfaces used in a second embodiment of a set of masks according to FIG. 2.
Figure 5B:
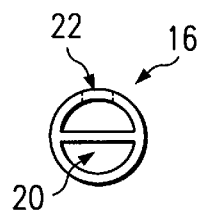
Figure 5C:
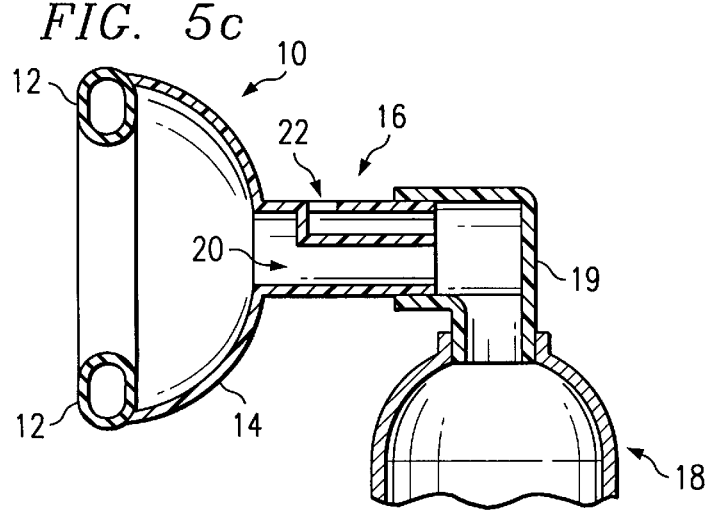
Figure 5D:
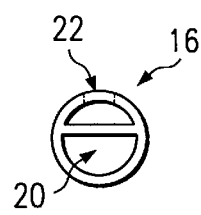
Figure 5E:
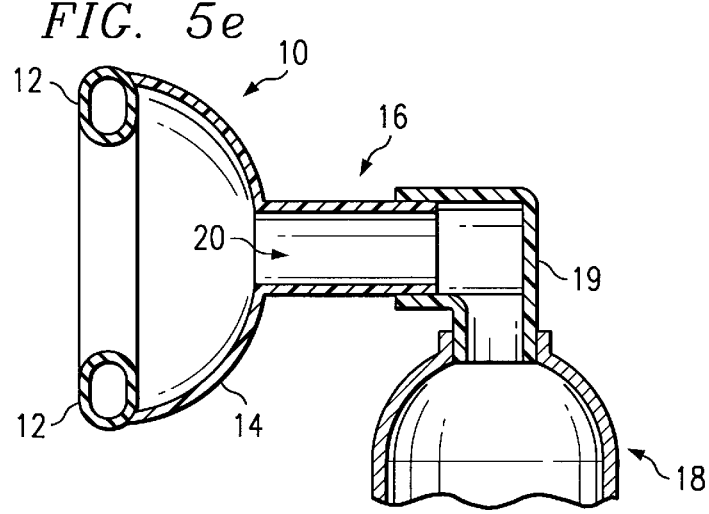
Figure 5F:
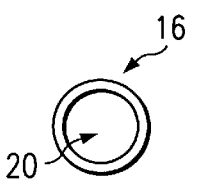

FIGS. 5a–f illustrate an alternative structure for the interface 16. FIGS. 5a–b illustrate a cross-section side view and a front view of an interface 16 for infant mask, FIGS. 5c–d illustrate a cross-section side view and a front view of an interface 16 for a child mask, and FIGS. 5e–f illustrate a cross-section side view and a front view of an interface 16 for an adult mask. In this embodiment, at the point of connection to the elbow joint 19, the cross-section of the interface 16 is split into two valves, the pass through valve 20 which is communication with the patient and the bypass valve 22 which vents the gas from the ventilation bag 18 to the exterior of the mask. In the preferred embodiment, the interface 16 for the adult mask passes all gas from the ventilation bag 18 to the patient.

Figure 6A:
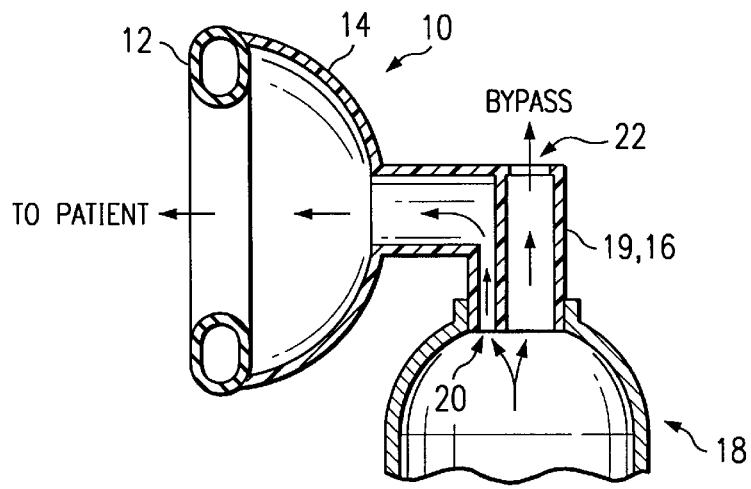
FIGS. 6a through 6c illustrate cross-sectional views of interfaces used in a third embodiment of a set of masks according to FIG. 2.
Figure 6B:
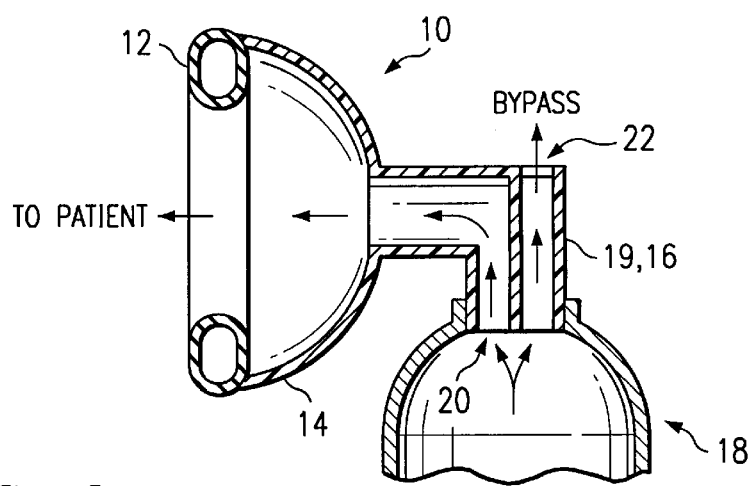
Figure 6C:
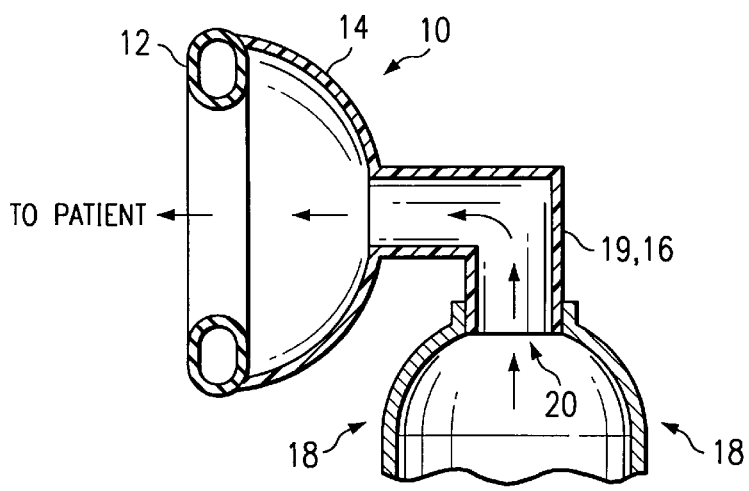

FIGS. 6a–c illustrate cross-sectional side views of a embodiment in which the interface 16 and elbow joint 19 are both integrated in the mask 10, and ventilation bag 18 is coupled to one of the masks 10 at the elbow joint 19. As before, a portion of the gas from the ventilation bag 18 vents though the bypass valve 22 to the exterior of the mask and the remaining gas passes through the pass through valve 20 to the patient. In the preferred embodiment, the interface 16 and elbow joint 19 for the adult mask does not need a bypass valve 22.

Figure 6D:
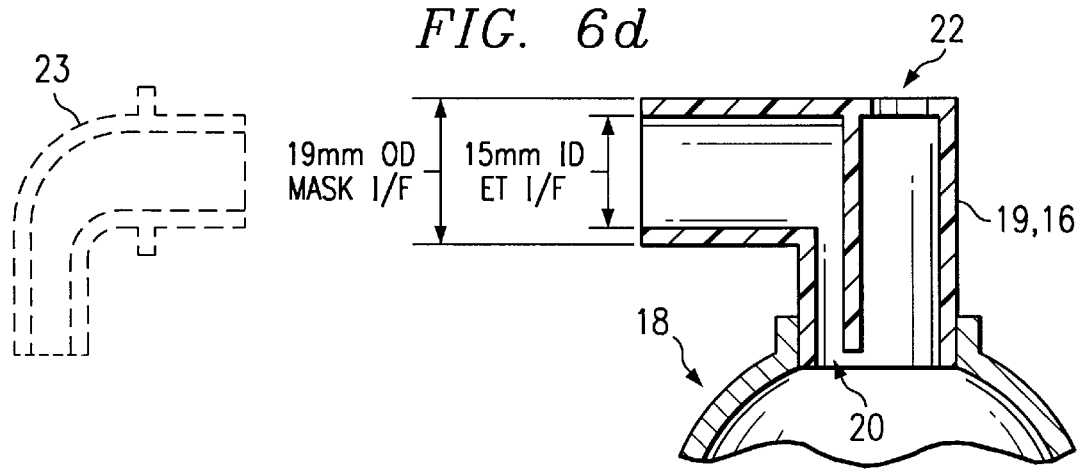
FIGS. 6d through 6f illustrate cross-sectional views of interfaces used in an embodiment of a mask/endotracheal tube combination.
Figure 6E:
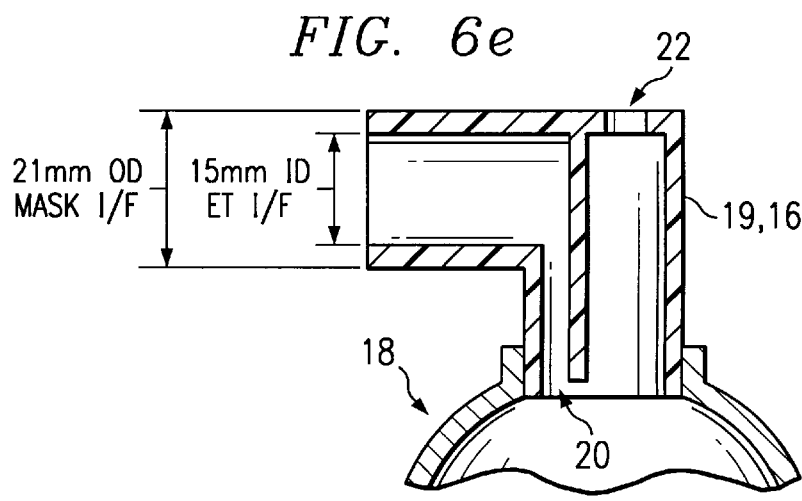
Figure 6F:
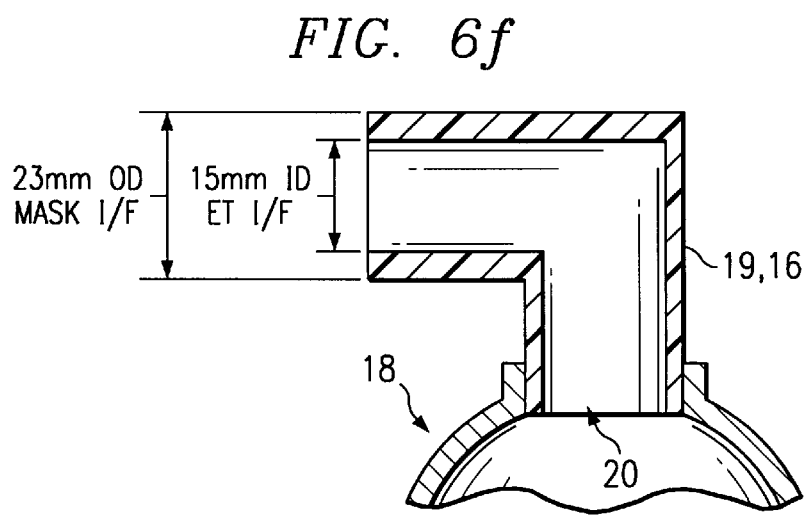

FIGS. 6d–6f illustrate a variation of the set of interfaces of FIGS. 6a–c, which allow safe use of an endotracheal tube as well as a mask. FIG. 6d illustrates the interface for infant, FIG. 6e illustrates an interface for a child and FIG. 6f illustrates an interface for an adult. As shown in connection with FIGS. 6a–c, each interface shown in FIGS. 6d–f passes gas from the ventilation bag 18 through the pass through valve 20 and the bypass valve 22 (as shown, the adult interface does not use a bypass valve) in a proportion which is appropriate for the patient. Each of the interfaces 16 shown in FIGS. d–f has a inner diameter of the point of connection to the mask/endotracheal tube of 15 mm. The outer diameter at this point varies dependent upon the intended patient size: the infant mask has an outer diameter of 19 mm, the child mask has an outer diameter of 21 mm and the adult mask has an outer diameter of 23 mm.

The interfaces 16 shown in FIGS. 6d–f allow a standard endotracheal tube to be inserted into the 15 mm interface. However, the face plate 14 of mask 10 will only fit the appropriate sized outer diameter of the interface; i.e., the face plate 14 of the infant mask will have a connection which fits with the 19 mm outer diameter of the interface 16, the face plate 14 of the child mask will have a connection which fits with the 21 mm outer diameter of the interface 16, and the face plate 14 of the adult mask will have a connection which fits with the 23 mm outer diameter of the interface 16.

In operation, the emergency personnel will attempt resuscitation using the appropriate sized mask for the patient. As described above, the correct size mask automatically direct the correct amount of gas from the ventilation bag 18 to the patient, so that a single ventilation bag size can be used for all patients. If necessary, an endotracheal tube 23 can be inserted into the interface 16. The interface will also control the amount of gas which passes through the endotracheal tube 23. There is not danger in putting an incorrectly sized mask on the interface 16, since only the correct sized mask will form a proper seal with the interface 16.

In the preferred embodiment, the interface 16 is integral with the swiveling elbow joint 19, although the interface could be made as a separate connecting part.

While the system of FIGS. 6d–f has been described using different interface diameters for interface with the masks, other means to connected to an appropriate mask size could be employed, such as using different shaped interfaces to connect only to the appropriate mask.

In FIGS. 3–6, all the gas from the ventilation bag 18 is directed towards an integral component of the mask 10. Thus each mask 10 in a set of masks of different sizes includes the mechanism to split the air from the ventilation bag 18 such that the patient receives the correct amount. FIGS. 7 and 8 illustrate embodiments where each mask 10 controls the amount of gas from the ventilation bag 18 which is directed to the patient, but where the bypass valve 22 is integral to the ventilation bag.

FIG. 7 illustrates a cross-sectional side view of a mask 10 and ventilation bag 18 where the bypass valve 22 is part of the elbow joint 19 connected to the ventilation bag 18. In this case, the bypass valve 22 does not need to be permanently attached to the mask 10, it can be attached at the time of use. However, the amount of air which passes to the patient is still controlled by the mask 10 which is attached to the elbow joint. While the size of the bypass valve is a constant, the size of the pass through valve 20 can be varied from mask to mask in the set to allow different portions of gas to pass to the patient, depending upon what size of mask is attached to the elbow joint 19. In this case, since some of the air will be diverted through the bypass valve 22 no matter which mask is being used, the ventilation bag should hold a quantity of air greater than needed to ventilate an adult. Alternatively, the mask 10 for an adult could include a blocking member to block the bypass valve 22 (see FIG. 8).

FIG. 8 illustrates a cross-sectional side view of another embodiment in which each mask in a set controls the size of a bypass valve 22 in the elbow joint 19, where the elbow joint is not permanently attached to the mask 10. In this embodiment, the length of interface 16 (which is attached permanently to each mask 10), or a portion of interface 16, can leave bypass valve 22 completely open (for and infant mask), partially open (for a child mask), or completely shut (for an adult mask). The greater the amount of closure of the bypass valve 22, the greater the portion of gas from the ventilation bag 18 that will be passed to the patient. While FIG. 8 shows a fixed-sized pass-through valve 20 for each mask in a set, the pass-through valve could also vary in size between masks.

The invention described herein provides significant advantages over the prior art. The set of masks 10 can fit, for example, infant, child and adult patients, respectively. A single ventilation bag, with a plurality of masks (and endotracheal tubes), can be taken together to the scene of an emergency, requiring very little space. Further, the invention can be used in hospitals to reduce storage space and simplify inventory maintenance.

While the invention has been described in connection with emergency medical personnel, it is also beneficial with regard to situations where relatively untrained people may be providing ventilation. For example, a kit with each mask size and a ventilation pump could be used at a pool site or at stations around a lake; since the correct volume of air is provided automatically by choosing the mask size which fits the patient, less trained personnel can resuscitate a patient without risk of injury.

Although the Detailed Description of the invention has been directed to certain exemplary embodiments, various modifications of these embodiments, as well as alternative embodiments, will be suggested to those skilled in the art. The invention encompasses any modifications or alternative embodiments that fall within the scope of the Claims.

I claim:

1. A manual resuscitation system comprising:
   a ventilation bag holding a known volume of a gas;
   a plurality of masks for individually coupling to said ventilation bag, each mask sized to fit an associated patient size and including means for transmitting a predetermined amount of gas to a patient responsive to a full squeeze of said ventilation bag, such that the amount of gas transmitted to a patient is dependent upon which of said masks is coupled to said ventilation bag.

2. The manual resuscitator of claim 1 wherein said ventilation bag holds a sufficient volume of gas to resuscitate an adult patient.

3. The manual resuscitator of claim 2 wherein one of said plurality of masks is associated with adult patients and passes all gas from said ventilation bag to a patient.

4. The manual resuscitator of claim 3 wherein others of said plurality of masks pass a portion of the gas from said ventilation bag to a patient.

5. The manual resuscitator of claim 4 wherein said other of said masks include a bypass valve which passes a portion of the gas from said ventilation bag to a patient.

6. The manual resuscitator of claim 5 wherein one of said other masks is a child mask.

7. The manual resuscitator of claim 5 wherein one of said masks is an infant masks.

8. The manual resuscitator of claim 1 wherein said plurality of masks nest inside one another during storage.

9. The manual resuscitator of claim 1 wherein each of said masks include an interface for controlling the amount of gas passed to a patient.

10. The manual resuscitator of claim 1 wherein one or more of said plurality of masks includes a bypass valve for releasing a portion of said air from said ventilation bag.

11. The manual resuscitator of claim 10 wherein said one or more of said plurality of masks further include a pass through valve for passing air from said ventilation bag to said mask.

12. The manual resuscitator of claim 11 wherein the relative sizes of the bypass valve and the pass through valve determine the portion of air passed from the ventilation bag to a patient.

13. The method of claim 10 wherein said choosing step comprises the step of choosing a mask from a set of masks each having an associated patient weight range.

14. A method of resuscitating a patient, comprising the steps of:

providing a plurality of masks of different sizes, each of which includes means for transmitting a predetermined amount of gas to a patient responsive to a full squeeze of an attached ventilation bag, choosing a mask which is the best fit for the patient from a set of differently sized masks;

connecting the mask to a ventilation bag;

applying the mask to the patient's face; and squeezing the ventilation bag to force air through the mask into the patient's lungs.

15. The method of claim 14 wherein said squeezing step comprises the step of squeezing a volume of air from said ventilation bag sufficient to resuscitate an adult patient.

16. The method of claim 14 wherein said choosing step comprises the step of choosing a mask from a set of adult, child and infant sized masks.

17. A manual resuscitation system comprising:

a ventilation bag holding a known volume of a gas;

a plurality of interfaces for individually coupling to the ventilation bag, each interface associated with a patient size and including means for transmitting a predetermined amount of gas through the interface to a patient responsive to a full squeeze of said ventilation bag, such that the amount of gas transmitted to a patient is dependent upon which of said interfaces is coupled to said ventilation bag;

a plurality of masks, each mask sized to fit an associated patient size, for coupling to a corresponding one of said interfaces, each mask mating only with its corresponding interface and not mating with other of said interfaces; and one or more endotracheal tubes for coupling to said interfaces.

18. The manual resuscitator of claim 17 wherein said one or more endotracheal tubes have a standard interface size.

19. The manual resuscitator of claim 17 wherein said masks each have a unique shaped connector for mounting with the corresponding interface.

20. The manual resuscitator of claim 17 wherein said interface is integral with a swiveling elbow joint.

* * * * *